(12) United States Patent
Yamamoto et al.

(10) Patent No.: US 6,755,952 B1
(45) Date of Patent: Jun. 29, 2004

(54) DEVICE FOR ELECTROPHORESIS

(75) Inventors: Kenji Yamamoto, Kanagawa (JP); Noriko Yurino, Kanagawa (JP)

(73) Assignee: Hitachi Software Engineering Co., Ltd., Kanagawa (JP)

(*) Notice: Subject to any disclaimer, the term of this patent is extended or adjusted under 35 U.S.C. 154(b) by 318 days.

(21) Appl. No.: 09/787,128

(22) PCT Filed: Jun. 27, 2000

(86) PCT No.: PCT/JP00/04210
§ 371 (c)(1),
(2), (4) Date: Mar. 13, 2001

(87) PCT Pub. No.: WO01/06247
PCT Pub. Date: Jan. 25, 2001

(30) Foreign Application Priority Data

Jul. 16, 1999 (JP) .......................................... 11-203646

(51) Int. Cl.[7] ........................ G01N 27/453; G01N 30/02
(52) U.S. Cl. .......................... 204/603; 204/601; 422/70
(58) Field of Search ................................ 204/451, 452, 204/601, 603; 356/344; 422/70

(56) References Cited

U.S. PATENT DOCUMENTS

| | | | | |
|---|---|---|---|---|
| 4,417,967 A | * | 11/1983 | Ledley ........................ | 204/466 |
| 5,376,252 A | * | 12/1994 | Ekstrom et al. ............. | 204/603 |
| 5,405,519 A | * | 4/1995 | Schwartz ..................... | 204/609 |
| 5,717,602 A | * | 2/1998 | Kenning ...................... | 700/266 |
| 5,728,528 A | * | 3/1998 | Mathies et al. ............... | 435/6 |
| 6,013,165 A | * | 1/2000 | Wiktorowicz et al. ....... | 204/456 |
| 6,028,190 A | * | 2/2000 | Mathies et al. ............. | 536/26.6 |
| 6,074,725 A | * | 6/2000 | Kennedy ..................... | 428/188 |

FOREIGN PATENT DOCUMENTS

| | | | | |
|---|---|---|---|---|
| EP | 0 581 412 | | 2/1994 | ......... G01N/27/447 |
| EP | 0 770 871 | | 5/1997 | .......... G01N/30/30 |
| EP | 0 840 113 | | 5/1998 | ......... G01N/27/447 |
| WO | WO 93/20435 | | 10/1993 | ......... G01N/27/447 |
| WO | WO 98/00583 | | 1/1998 | ........... C25B/15/02 |

OTHER PUBLICATIONS

Pace et al. ("Relation of molecular weight to electrophoretic mobility of fluorescamine–labeled proteins in polyacrylamided gels," Biochemical and Biophysical Research Communications (1974), 57(2), 482–7).*

Fan et al. ("Study of Joule heat in the separation by high–performance capillary electrophoresis," Zhongguo Yaoke Daxue Xuebao (1996), 27(2), 87–90).*

Slater et al. ("Diffusion, Joule heating, and band broadening in capillary gel electrophoresis of DNA," Electrophoresis (1995), 16(1), 75–83).*

McGregor, D.A., et al., "*Interactive Control of Pulsed Field Gel Electrophoresis via Real Time Monitoring*," Analytical Chemistry, American Chemical Society, vol. 64, No. 1 (1992), pp. 1–6.

* cited by examiner

*Primary Examiner*—Alex Noguerola
(74) *Attorney, Agent, or Firm*—Reed Smith LLP; Stanley P. Fisher, Esq.; Juan Carlos A. Marquez, Esq.

(57) ABSTRACT

The present invention allows detection in short time while maintaining the level of the resolving power as high as when a capillary is utilized.

The entire surface of an electrophoresis board 10, which is provided with a two-dimensional tubular electrophoresis pathway, is irradiated with excitation light so as to pick up fluorescence or luminescence from a sample with a two-dimensional sensor. By reading the entire electrophoresis pathway, the separated state of the sample may be confirmed during the electrophoresis. As a result, the electrophoresis may be ended when the sample is sufficiently separated and a molecular weight thereof may be determined based on the migration distance.

8 Claims, 11 Drawing Sheets

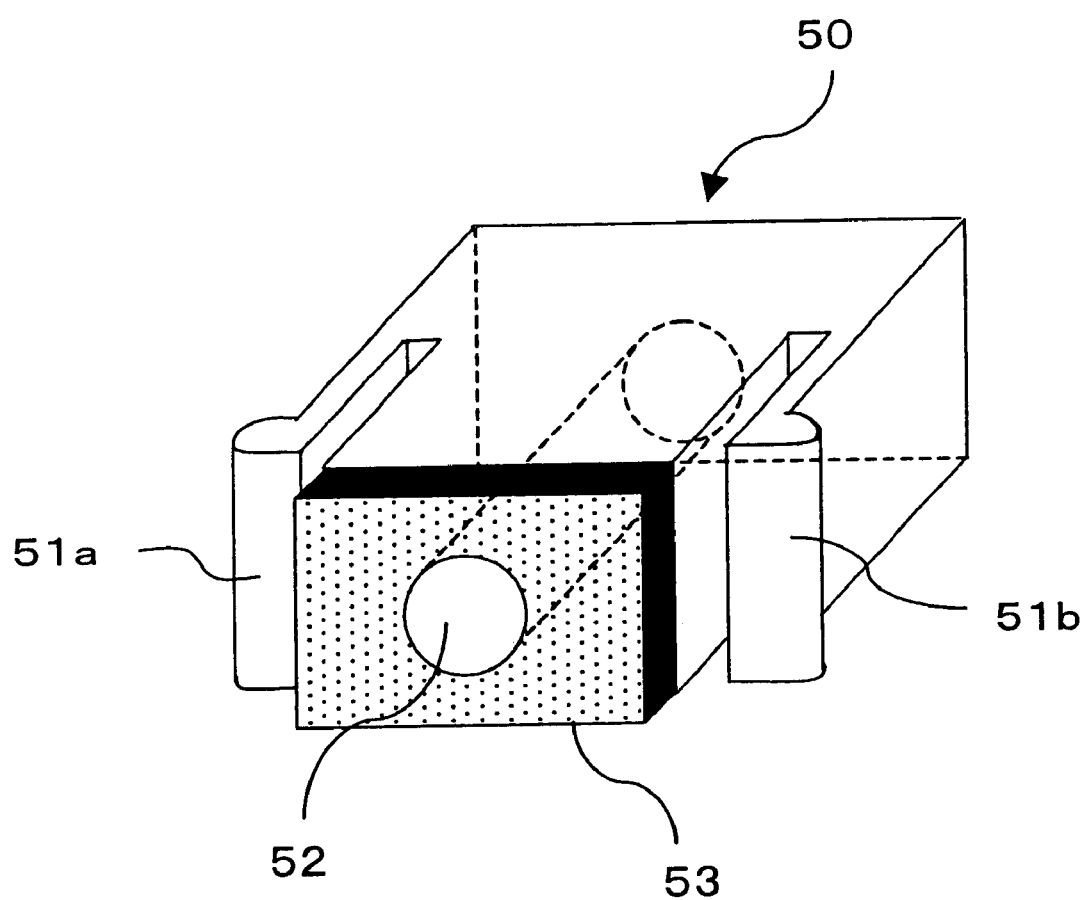

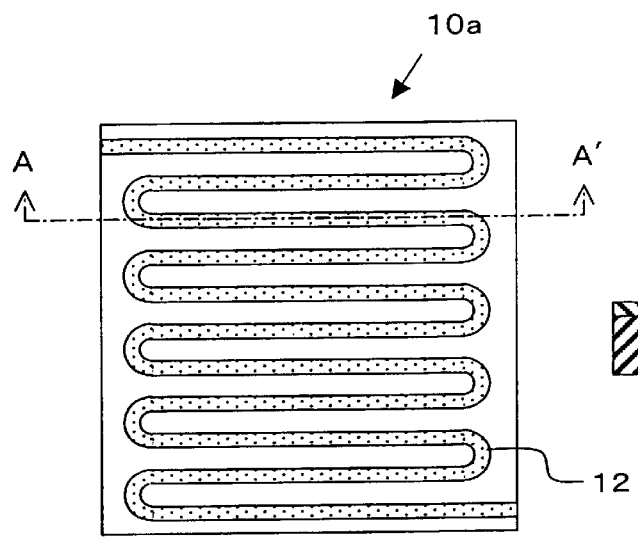
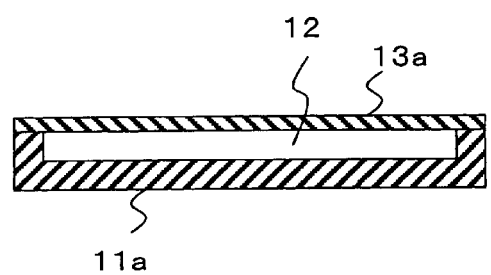
Fig. 5A  Fig. 5B
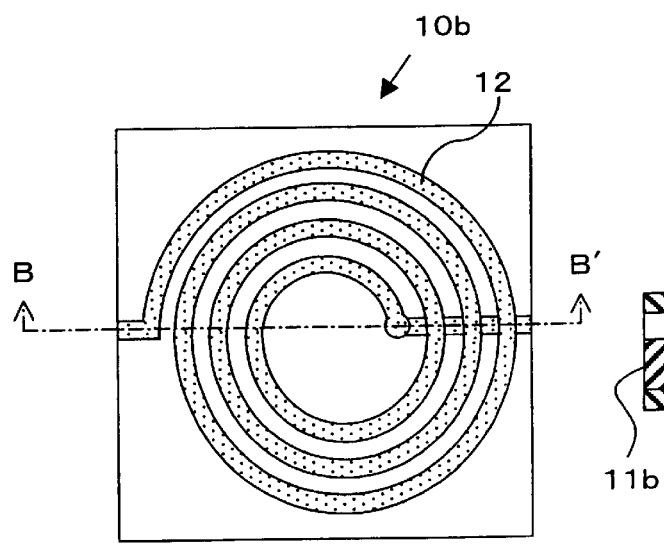
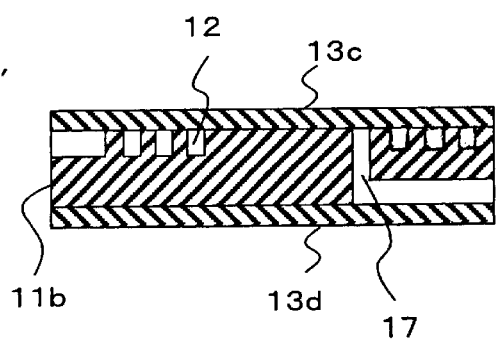
Fig. 6A  Fig. 6B

Band A   81   82

Band A

Light intensity

Migration distance of Band A

Migration distance

Light intensity

Migration distance

Short ← Electrophoresis time → Long

Rectangular ▭ : zooming
Double click

⊕ : Point zooming
Shift+⊕

Band
[k]: selection

[M]: Partial profile display

DEVICE FOR ELECTROPHORESIS

TECHNICAL FIELD

The present invention relates to a method and a device for electrophoresis by and with which a fluorescence- or chemiluminescence-labeled biological sample such as DNA or a protein is separated and detected.

BACKGROUND ART

Electrophoresis is a method for separating a biological sample such as DNA or a protein according to its molecular weight. Among such electrophoresis, capillary electrophoresis is known as a method having an enhanced sample resolving power.

FIGS. 12A and 12B are illustrations of an exemplary electrophoresis device using a gel-injected capillary. First, as shown in FIG. 12A, one end of the capillary 121 injected with a gel 122 is immersed in a sample solution 123 containing DNAs to be separated while the other end is immersed in a buffer bath 124. A voltage is applied from a power source 125 to the sample solution 123 and the buffer bath 124 such that the potential of the sample solution 123 is negative while the potential of the buffer bath 124 is positive. Since DNAs 127 are negatively-charged, they migrate toward the high potential end and enter into the gel 122 of the capillary 121. Next, as shown in FIG. 12B, the end of the capillary 121 immersed in the sample solution is replaced in a buffer bath 126 with a negative potential such that the buffer bath 124 with the other end of the capillary 121 immersed has a positive potential. A voltage is continuously applied from the power source 125 to the buffer bathes 126 and 124 to direct the DNAs 127 to migrate through the gel 122 toward the high potential end as represented by an arrow. Since DNA 127a with a smaller molecular weight migrates faster than DNA 127b with a larger molecular weight, DNAs may be separated according to their molecular weights. The separated DNAs 127a and 127b may be detected by irradiating fluorescent labels pre-bound to the DNAs with excitation light 132 from a light source 131, and detecting the fluorescence emitted from the excited fluorescent label with a photosensor 133. In this manner, molecular weights of the DNAs 127 are determined based on the time required from the initiation of the electrophoresis for each of the DNAs to arrive at a detection point (the position of radiating the excitation light).

As described above, capillary electrophoresis determines a molecular weight of a sample component based on the time required from the initiation of the electrophoresis for the component to arrive at a detection point fixed on an electrophoresis pathway. Therefore, even when the components are sufficiently separated before they reach the detection point, electrophoresis has to be continued until all of the components arrive at the detection point. Components with smaller molecular weights have larger mobility and thus arrive at the detection point at an earlier stage. On the other hand, as the molecular weight becomes larger, the mobility becomes smaller in inverse proportion to the logarithm of the molecular weight. As a result, the time required for the component to reach the detection point becomes longer, and thus requiring long time for separation and detection.

The capillary used for capillary electrophoresis is a narrow fused silica tube with inner and outer diameters of as small as 25–100 $\mu$m and 100–200 $\mu$m, respectively, which can very easily be broken. Accordingly, the outer surface of the tube is usually coated with polyimide for reinforcement. Since this polyimide coating, however, prevents sufficient excitation light to enter inside the capillary and prevents sufficient fluorescence to come out, the polyimide coating at the detection point is peeled off. Since it is difficult to read the entire capillary, the sample has to be separated and detected after a predetermined electrophoresis time to determine the molecular weight.

Furthermore, although the capillary is coated with polyimide, it cannot be bent for more than a predetermined curvature. Accordingly, some capillaries used, depending on their lengths, may be difficult to be handled with and may require a large space for setting, rendering miniaturization of the device difficult. In the case of SSCP (Single Strand Conformation Polymorphism) method which requires electrophoresis to be carried out while maintaining an electrophoresis pathway at a predetermined temperature, the temperature of the capillary stretching over a large area needs to be controlled. This requires a very expensive controlling mechanism, rendering this method unpractical.

The present invention has an objective of providing an electrophoresis method and an electrophoresis device which have the same resolving power as when a capillary is used and which allow detection in a shorter time. The present invention also has an objective of providing a compact electrophoresis device whose electrophoresis pathway can be controlled of its temperature with high accuracy.

In order to accomplish the above-described objectives, the electrophoresis device of the invention typically comprises: an electrophoresis board provided with a two-dimensional tubular electrophoresis pathway formed by laminating a plane plate on a plate provided with a narrow groove; an excitation light source capable of radiating excitation light to the entire surface of the electrophoresis board; a two-dimensional sensor for receiving fluorescence or luminescence; and a means for controlling the temperature of the entire surface of the electrophoresis board.

By using the above-described means, the following can be realized. The separated state of a sample can be confirmed during the electrophoresis by reading the entire electrophoresis pathway. Accordingly, there is no need of conducting electrophoresis for a long time than is necessary. The electrophoresis may be ended when the sample has sufficiently been separated to determine the molecular weight by measuring the migration distance. As a result, separation and detection may be conducted within a minimum time. For example, when an electrophoresis pathway with a width of 100 $\mu$m is formed in an electrophoresis board, the length of the pathway may be about 2 m within an area of 2 cm$^2$. Accordingly, a compact device can be realized with an inexpensive temperature controlling system. As a result, temperature of the entire electrophoresis pathway can accurately be controlled with a low-cost mechanism.

An electrophoresis method of the invention comprises the steps of: subjecting a fluorescence-labeled sample to electrophoresis through a two-dimensional electrophoresis pathway; and radiating excitation light to the entire electrophoresis pathway to simultaneously detect luminescence emitted from the fluorescent label of the migrating sample with a two-dimensional sensor.

Another electrophoresis method of the invention comprises the steps of: subjecting a mixture, which contains a fluorescence-labeled sample and a substance as an excitation energy donor for the fluorescent substance, to electrophoresis through a two-dimensional electrophoresis pathway; and simultaneously detecting luminescence emitted from the fluorescent label of the migrating sample with a two-dimensional sensor.

According to these electrophoresis methods, there is no need of performing electrophoresis until all of the sample components to be detected reach the detection point as in conventional methods. Molecular weights of the sample components may be determined based on the migration distances when the sample components are sufficiently separated.

An electrophoresis device of the present invention comprises: an electrophoresis board provided with a narrow tubular electrophoresis pathway; an excitation light source for radiating excitation light to the entire electrophoresis board; and a two-dimensional sensor for receiving luminescence emitted from the sample irradiated by the excitation light source and migrating through the electrophoresis pathway. The sample is simultaneously detected from the entire electrophoresis pathway by the two-dimensional sensor. This electrophoresis device may be employed for electrophoresis of a fluorescence-labeled sample.

Another electrophoresis device of the present invention comprises: an electrophoresis board provided with a narrow tubular electrophoresis pathway; and a two-dimensional sensor for receiving luminescence emitted from the sample migrating through the electrophoresis pathway. The sample is simultaneously detected from the entire electrophoresis pathway by the two-dimensional sensor. This electrophoresis device may be employed for electrophoresis of a chemiluminescence-labeled sample.

The electrophoresis device of the invention may further comprise an image displaying means for displaying an image picked up by the two-dimensional sensor. The degree of separation of the sample may be observed by an electrophoresis image displayed on the image displaying means.

The electrophoresis device of the invention may further comprise a light intensity profile displaying means for displaying a profile of the intensity of the luminescence detected by the two-dimensional sensor as a function of a distance along the electrophoresis pathway. A profile of luminescence intensity may be obtained by processing an electrophoresis image picked up by the two-dimensional sensor and extracting migration distances along the electrophoresis pathway and light intensities at each of the migration distances.

The electrophoresis device of the present invention may further comprise: an image displaying means for displaying an image picked up by the two-dimensional sensor; and a light intensity profile displaying means for displaying a profile of the intensity of the luminescence detected by the two-dimensional sensor as a function of a distance from the initiating position of the electrophoresis pathway.

Preferably, the electrophoresis device of the invention comprises: a selecting means for selecting a part of sample bands on the electrophoresis image displayed on the image displaying means; and a light intensity profile zooming means for zooming the profile of the light intensity of the sample band selected by the selecting means.

Furthermore, the electrophoresis device of the invention may further comprise: a selecting means for selecting a sample band on the electrophoresis image displayed on the image displaying means; and a means for indicating a peak point of the light intensity profile corresponding to the sample band selected by the selecting means. By using the above-mentioned means, relationship between the sample bands on the electrophoresis image and peaks in the light intensity profile may readily be found out. As a result, separated states of bands can easily be confirmed.

The image displaying means, the light intensity profile displaying means, light intensity profile zooming means may have an independent display device. Alternatively, they may selectively displayed in turn or partitioningly be displayed on a monitor connected to the electrophoresis device or a monitor connected to a computer for controlling the electrophoresis device.

The electrophoresis pathway formed on the electrophoresis board has a shape formed with multiple linear parts, a shape formed with only curved parts or a shape formed with both linear and curved parts. Moreover, the electrophoresis device of the invention may further comprise a temperature controlling means for maintaining the entire surface of the electrophoresis board at a predetermined temperature.

BRIEF DESCRIPTION OF THE DRAWINGS

FIG. 3 is an isometric view showing an exemplary connector used for connecting the electrophoresis board with a communication tube;

FIGS. 5A and 5B are views for illustrating an exemplary pattern of an electrophoresis pathway;

FIGS. 6A and 6B are views for illustrating another exemplary pattern of an electrophoresis pathway;

BEST MODE FOR CARRYING OUT THE INVENTION

Hereinafter, embodiments for carrying out the present invention will be described with reference to the drawings.

Figure 1:
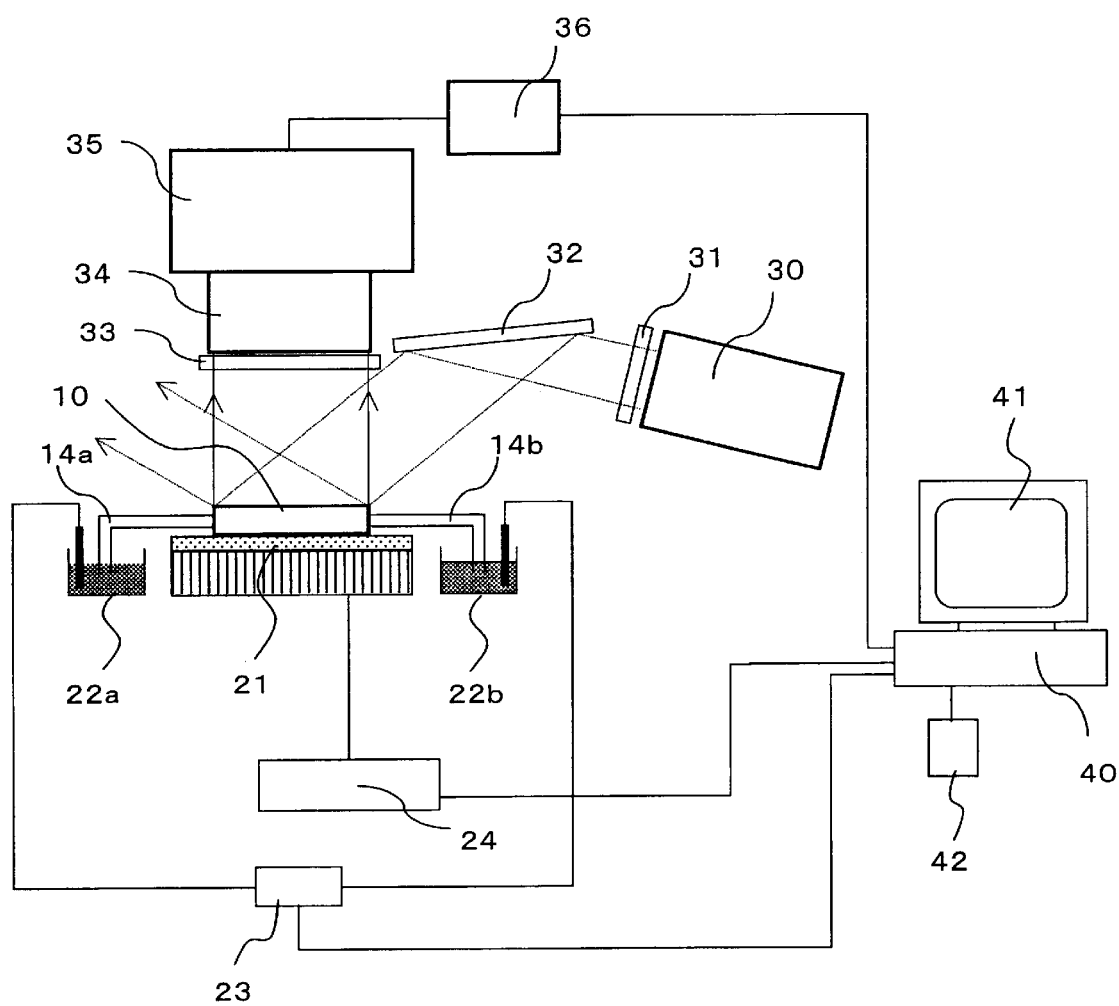
FIG. 1 is a schematic view showing an exemplary electrophoresis device of the present invention.

FIG. 1 is a schematic view showing an exemplary electrophoresis device of the present invention. FIGS. 2 to 6 are views for illustrating structures of an electrophoresis board of the present invention.

Figure 2A:
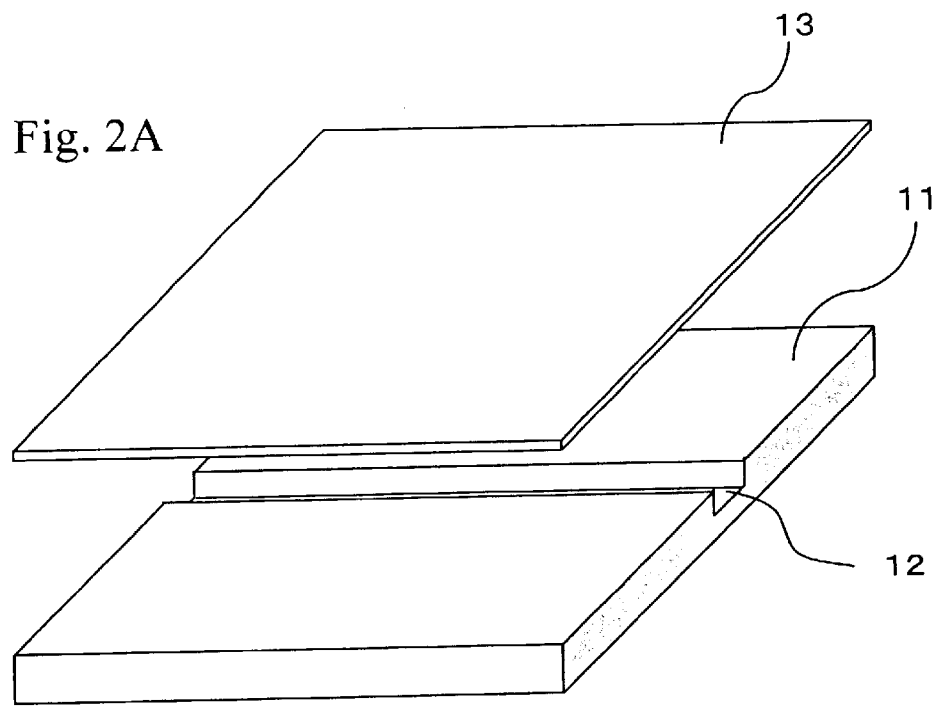
FIGS. 2A and 2B are views for illustrating a basic structure of an electrophoresis board.
Figure 2B:
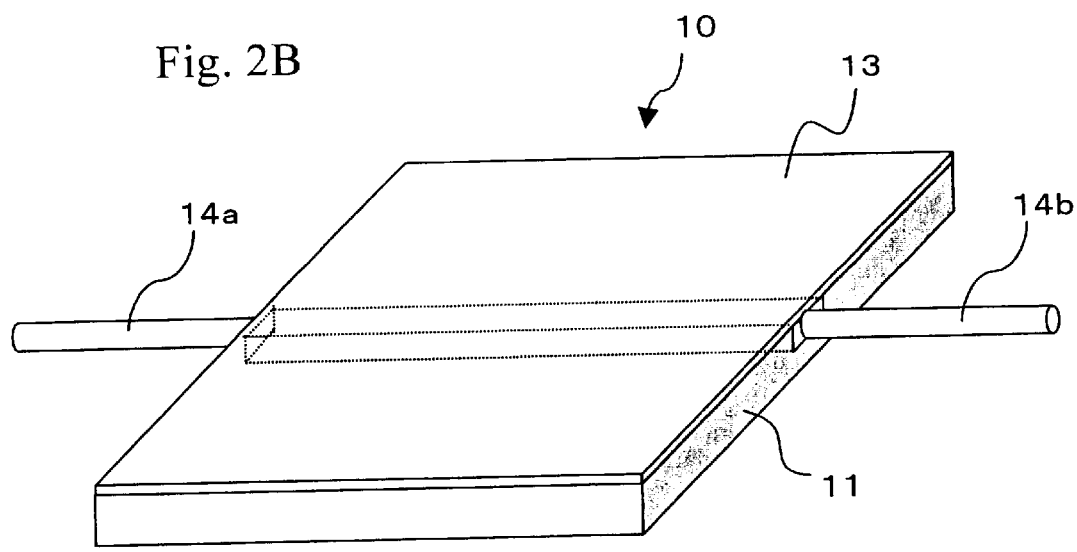

First, exemplary structures of the electrophoresis board of the invention will be described with reference to FIGS. 2 to 6. FIGS. 2A and 2B are views showing a basic structure of the electrophoresis board of the invention. FIG. 2A is an exploded view of the electrophoresis board; and FIG. 2B is an isometric view of the electrophoresis board. As shown in FIG. 2A, the electrophoresis board 10 comprises a plane plate 11 made of a glass material and a transparent cover plate 13. The surface of the plane plate 11 is provided with a groove (an electrophoresis pathway 12) by etching or the like. The width of the electrophoresis pathway 12 is about 100 $\mu$m, which is the same as the width of a capillary used for typical capillary electrophoresis. Unlike capillaries, the cross-sectional shape of the electrophoresis pathway is rectangular for measurement convenience. The surface of the plane plate 11 with the electrophoresis pathway 12 is covered with the cover plate 13, thereby forming the electrophoresis board 10. As shown in FIG. 2B, both ends of the electrophoresis pathway 12 are provided with communication tubes 14a and 14b for communicating the electrophoresis board 10 with buffer bathes 22a and 22b (see FIG. 1). Although the communication tubes 14a and 14b are connected to the sides of the electrophoresis board 10 in FIG. 2B since the ends of the electrophoresis pathway are located besides the electrophoresis board 10, they may be attached to the upper or bottom surface of the electrophoresis board 10 when the ends of the electrophoresis pathway are located at the upper or bottom surface of the electrophoresis board 10.

Figure 4A:
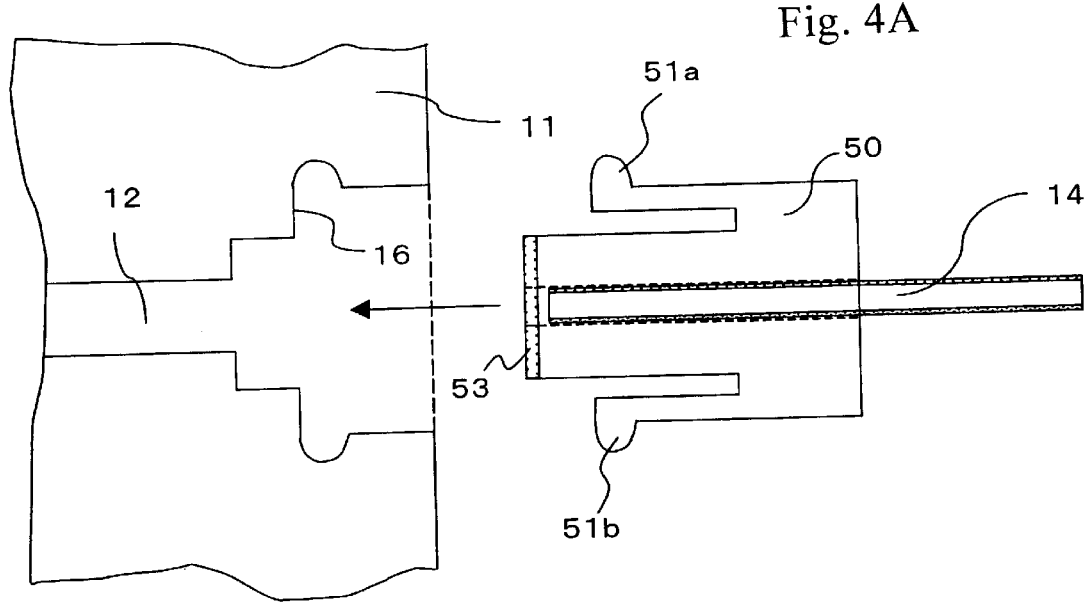
FIGS. 4A and 4B are schematic views for illustrating a way of connecting the communication tube with the electrophoresis pathway.
Figure 4B:
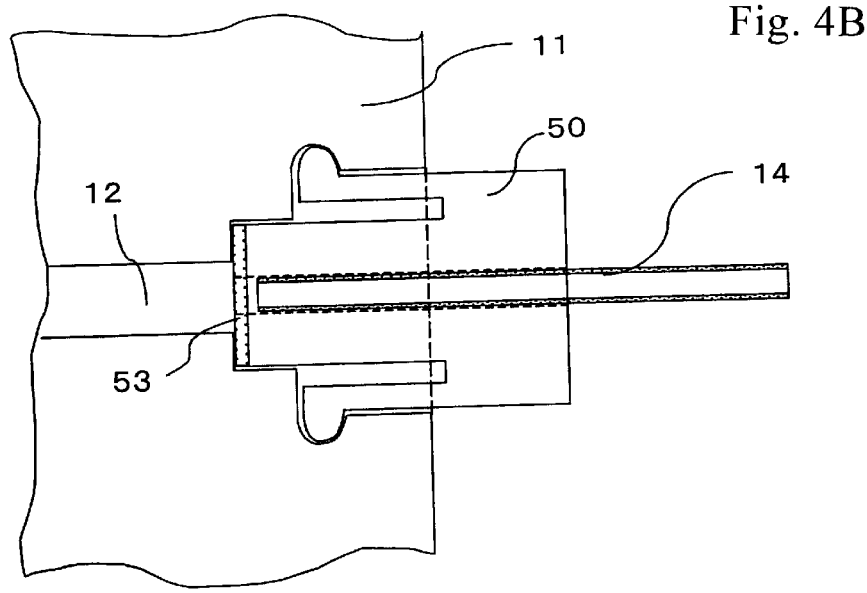

With reference to FIGS. 3 and 4A–4B, an exemplary method for connecting a communication tube 14 to the electrophoresis board 10 will be described. FIG. 3 is an isomeric view showing an exemplary connector 50 used for connecting the communication tube 14 to the electrophoresis board 10. FIGS. 4A and 4B are schematic views for illustrating a method for connecting the communication tube by using the connector 50 shown in FIG. 3.

As shown in FIG. 3, the connector 50 is provided with detents 51a and 51b on both sides for anchoring itself to the electrophoresis board 10, and is provided with a through hole 52 penetrating the center of the connector for inserting the communication tube 14 therein. The detents 51a and 51b are able to bend inside to some extent due to the flexibility of the material such that the space between the detents 51a and 51b becomes narrow. The surface that makes contact with the electrophoresis board 10 (the plane plate 11) is sealed with a silicon rubber packing 53 for preventing a liquid leak.

As shown in FIG. 4A, the communication tube 14 is inserted into the through hole 52 of the connector 50 and fixed therein with an adhesive or the like. Upon etching the electrophoresis pathway 12 in the plane plate 11 of the electrophoresis board 10, the end portion 16 of the electrophoresis pathway 12 is processed into a shape corresponding to the outer shape of the connector 50 as shown in FIG. 4A. As shown in FIG. 4B, the plane plate 11 of the electrophoresis board 10 and the communication tube 14 are connected by inserting the connector 50 into the end portion 16 of the electrophoresis pathway 12. The connector 50 is anchored to the electrophoresis board 10 by fitting the detents 51a and 51b into the corresponding concave parts formed at the end 16 of the electrophoresis pathway 12 in the plane plate 11 of the electrophoresis board 10. The gap between the end portion 16 of the electrophoresis pathway 12 and the connector 50 is sealed with the silicon rubber packing 53. For performing electrophoresis, the communication tube 14 is connected to the electrophoresis board 10 while, depending on the purpose, polyacrylamide is injected and gelatinized, or an electrophoresis buffer such as a phosphate buffer is injected through the electrophoresis pathway 12.

FIGS. 5A–5B and 6A–6B are views showing exemplary patterns of the electrophoresis pathway 12. In order to realize a longer migration distance within a smaller area, the pattern of the electrophoresis pathway 12 is, rather than a linear pattern extending from one end of the electrophoresis board to the other as shown in FIGS. 2A and 2B, advantageously a pattern that make the most of the entire area of the electrophoresis board. Examples of such patterns include a pattern formed with multiple linear parts, a pattern formed with only curved parts and a pattern formed with both linear and curved parts arranged as a single wave with a plurality of turns (FIG. 5A).

An electrophoresis board 10a shown in FIG. 5A has an electrophoresis pathway 12 whose pattern consists of linear and curved parts. The electrophoresis pathway 12 is formed on the upper surface of a plane plate 11a on which a cover plate 13a is fixed by means of adhesive or the like. FIGS. 5A is a plan view; and FIG. 5B is a cross-sectional view cut along line A—A' shown in FIG. 5A. When the electrophoresis pathway 12 lies in a zigzag line as shown in FIG. 5A, a pathway of about 2 m may be formed within an area of 2 cm$^2$.

An electrophoresis board 10b shown in FIG. 6A has a spirally-patterned electrophoresis pathway 12 consisting of only curved parts arranged as a single spiral. FIG. 6A is a plan view; and FIG. 6B is a cross-sectional view cut along line B—B' shown in FIG. 6A. As shown in FIG. 6B, the electrophoresis board 10b comprises a plane plate 11b whose upper and bottom surfaces are provided with grooves as the electrophoresis pathway 12, and cover plates. 13c and 13d sandwiching the plane plate 11b therebetween. The grooves in the upper and bottom surfaces of the plane plate 11b communicates via a through hole 17 penetrating through the plane plate 11b. At least the cover plate 13c on the detection side needs to be transparent.

Hereinafter, an exemplary structure of an electrophoresis device of the invention will be described with reference to FIG. 1. An electrophoresis board 10 is mounted on a thermostatic block 21 upon use. According to this example, the temperature of the thermostatic block 21 is controlled by using a Peltier element. The temperature of the electrophoresis board 10 upon electrophoresis varies depending on the sample to be treated. For example, the temperature of the electrophoresis board 10 should be adjusted to about 60° C. for DNA sequencing, or to a temperature that causes a difference in conformations (e.g., about 37° C.) for an analysis such as SSCP method that utilizes difference in the electrophoresis rates caused by a structural mutation in a single DNA strand. The temperature of the thermostatic block 21 is controlled by a temperature controller 24 which is given directions from a computer 40. Both ends of the electrophoresis board 10 communicates with buffer bathes 22a and 22b via communication tubes 14a and 14b, respectively. Electrophoresis is carried out by applying a voltage of about 15 kV from an electrophoresis power source 23 to the buffer bathes 22a and 22b.

The upper surface of the electrophoresis board 10 is entirely irradiated with excitation light from an excitation light source 30. For example, the excitation light is generated from a halogen lamp as a light source, made into a parallel luminous flux by an optical system, passed through an optical filter 31 where only light with a wavelength optimum for excitation of a fluorescent substance bound to a sample is transmitted, and directed to the electrophoresis board 10. The incident angle of the excitation light is adjusted with a reflecting mirror 32 so that light reflected of the upper surface of the electrophoresis board 10 does not directly enter the light-receiving system. According to this example, the electrophoresis sample is labeled with fluorescent substances, Cy3 (excitation wavelength: 550 nm, fluorescence wavelength: 570 nm) and Cy5 (excitation wavelength: 649 nm, fluorescence wavelength: 670 nm).

Fluorescence emitted from a fluorescent substance first passes through a light-receiving optical filter 33 where only light with the fluorescent wavelength is selectively transmitted, then converged by a light-receiving optical system 34 and finally form an image on a two-dimensional sensor 35. According to this embodiment, the two-dimensional sensor 35 is an inch-square air-cooling type CCD. The light-receiving optical system was arranged such that 1:1 image formation is realized at the light-receiving optical system 34. The output from the two-dimensional sensor 35 is sent to the computer 40 via a camera controller 36. The computer 40 is connected with an input means 42 such as a mouse or a keyboard, and a monitor 41. The input means 42 is used to enter electrophoresis conditions as well as to monitor the separated state of the migrating sample on the monitor 41 and to analyze the separated sample.

Where chemiluminescence is to be employed for reading, an electrophoresis sample is labeled with a fluorescent substance such as fluorescein isothiocyanate (FITC) or rhodamine. A substance that acts as an excitation-energy donor of the fluorescent substance, such as dioxetane or water-soluble oxamide, an oxalate derivative, is added to an electrophoresis buffer to chemically illuminate the fluorescent substance. Where the detection is to be conducted by a method that utilizes no excitation light such as chemiluminescence, the excitation light source 5 is switched off. Device components other than the excitation light source 5 are the same as those used for fluorescence-labeled samples.

Figure 7:
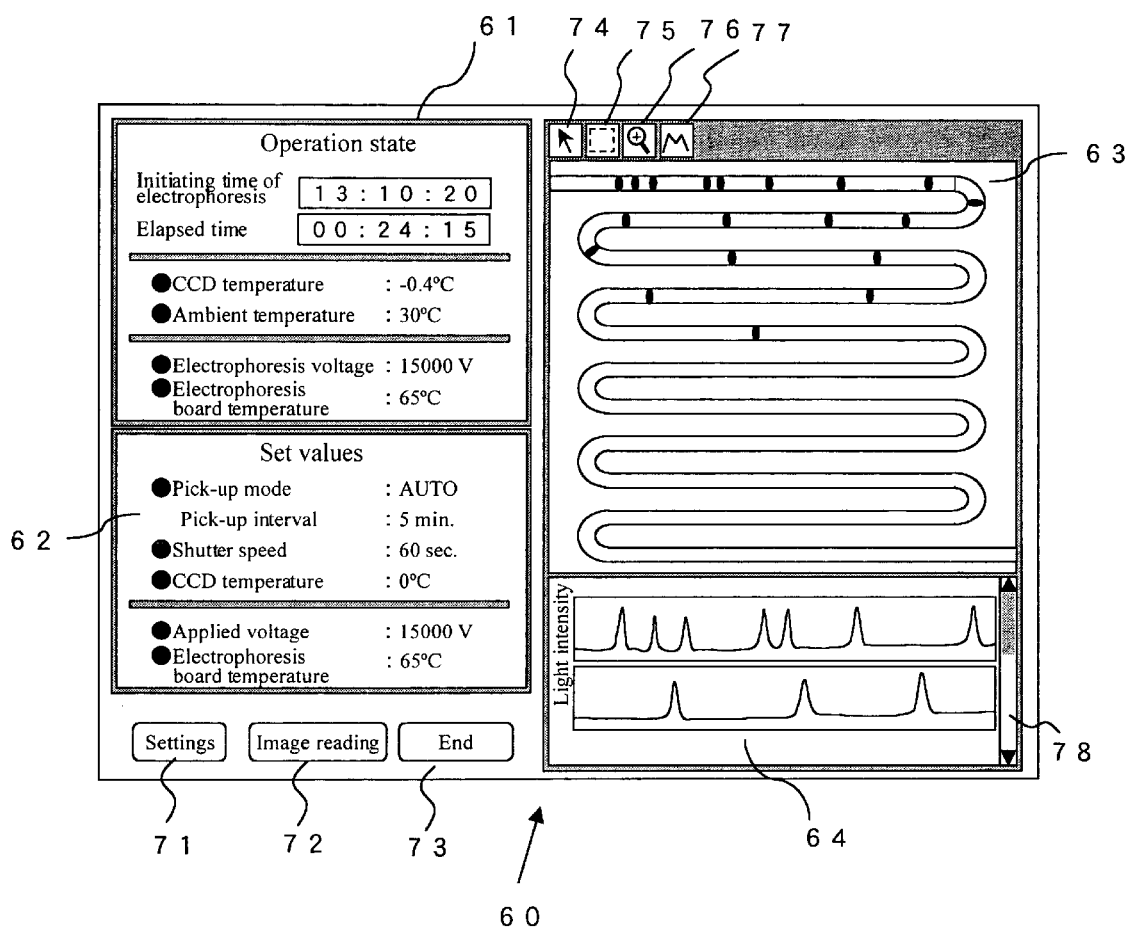
FIG. 7 is a view for illustrating an exemplary monitor screen.

FIG. 7 is a view showing an exemplary screen displayed on the monitor 41 connected to the computer 40. The monitor screen 60 includes an operation state displaying section 61 for displaying the operation state of the electrophoresis device in real time; a set value displaying section 62 for displaying conditions set for reading; an image displaying section 63 for displaying an electrophoresis image picked up by the two-dimensional sensor 35; a light intensity profile displaying section 64 for displaying a profile obtained by tracing the picked up image; and the like. The operation state displaying section 61 displays the initiating time of the electrophoresis, elapsed time from the initiating time of the electrophoresis, a temperature of the two-dimensional sensor (CCD) 35, an ambient temperature, an electrophoresis voltage, a temperature of the electrophoresis board 10, and the like. The set value displaying section 62 displays set values such as the pick-up mode, the shutter speed upon pick-up, the temperature of the CCD, the voltage applied from the electrophoresis power source 23 to the buffer bathes 22a and 22b and the temperature of the electrophoresis board 10. These set values may be altered by switching the operation mode to a set value input mode by pressing "Settings" button 71 and manipulating the input means 42 connected to the computer 40.

The image displaying section 63 displays an electrophoresis image picked up by the two-dimensional sensor 35 according to the conditions set for the "Pick-up mode" selected on the set value displaying section 62. When the "Pick-up mode" is in an "AUTO" mode, images are automatically picked up and up-dated on the screen according to the "Pick-up interval" (5 minutes in the figure) designated by the set value. When the "Pick-up mode" is in a "MANUAL" mode, the two-dimensional sensor 35 picks up an image as an "Image reading" button 72 is pressed and the picked up electrophoresis image is displayed. The light-intensity profile displaying section 64 displays a profile obtained by tracing the read image. An "End" button 73 is pressed when the separated state of the bands is sufficient and the monitor screen 60 is to be ended. When the "End" button 73 is pressed, the latest picked up image is immediately stored in a file and the monitor screen 60 is closed.

The electrophoresis pathway of the electrophoresis device of this embodiment is about 2 m and thus it is difficult to display the profile of the entire electrophoresis pathway on the displaying section 64. Accordingly, only a part of the electrophoresis pathway is displayed on the displaying section 64. The profile of a desired part may be displayed by scrolling the display screen with a slider 78 provided at the right of the displaying section. It is also difficult to confirm the separated states in minute parts if the image of the entire electrophoresis pathway is displayed on the image displaying section 63. Accordingly, a band selecting tool 74, a rectangular zooming tool 75, a point zooming tool 76 and a partial profile displaying tool 77 are provided as tools for confirming the separated state. By using these tools, a separated state of a sample may readily and efficiently be confirmed as described below. Similarly, the image displaying section 63 may display, rather than the image of the entire electrophoresis pathway, only a part of the electrophoresis pathway, where an image of the desired part may be displayed by scrolling the screen.

Figure 8A:
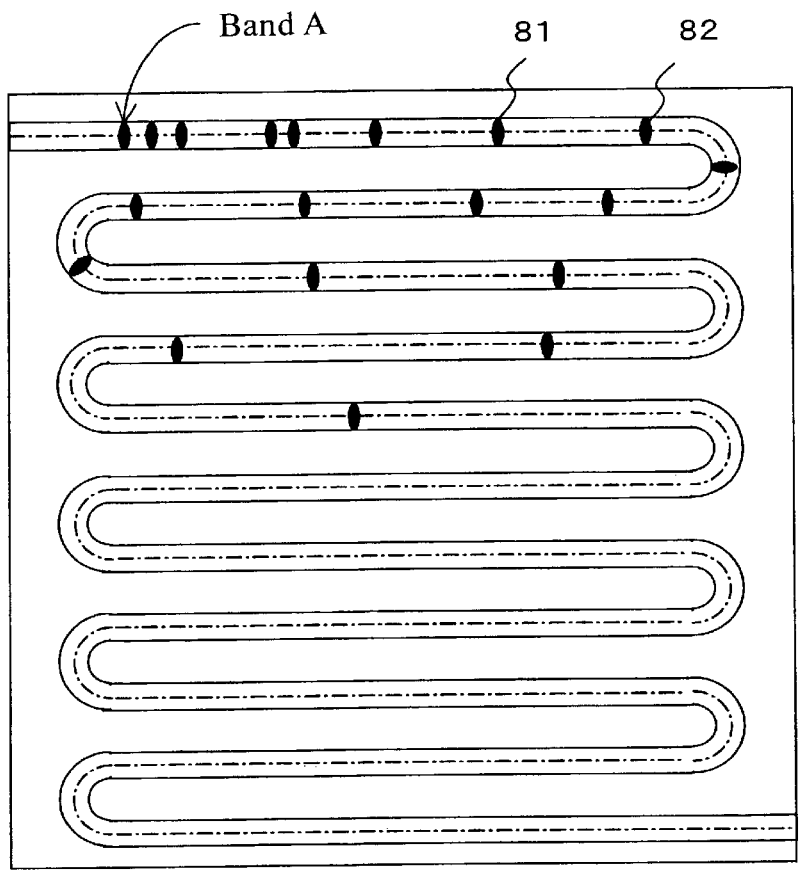
FIGS. 8A and 8B are views for illustrating a way of confirming the separated state.
Figure 8B:
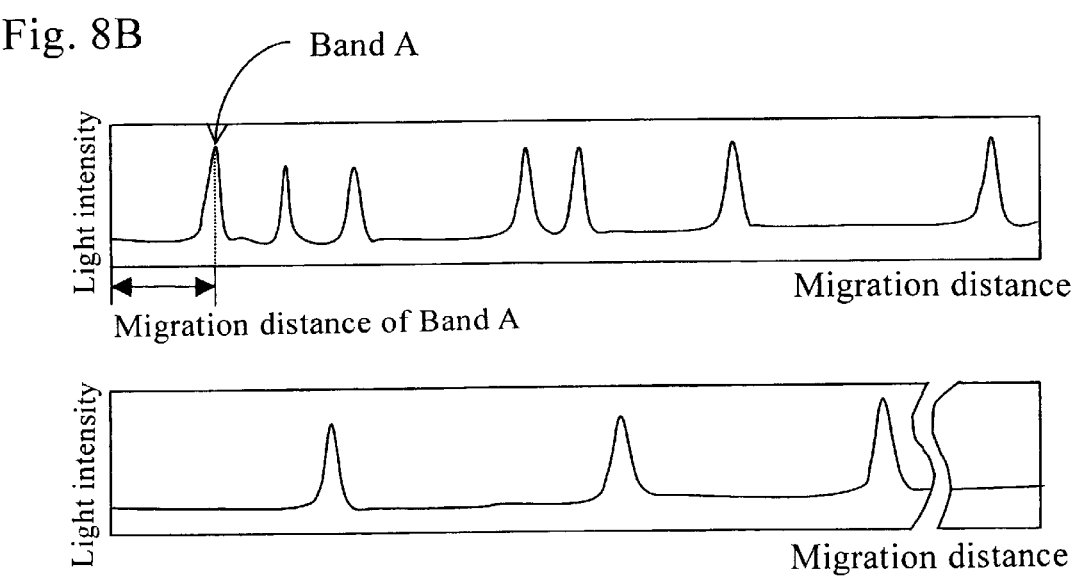

FIGS. 8A and 8B show an exemplary image read by the electrophoresis device of the invention, and an exemplary profiles of the fluorescence intensity, respectively. FIG. 8A shows an exemplary image displayed on the image displaying section 63 of the monitor screen 60. Sample bands 81 and 82 separated by the electrophoresis are shown as solid dots on the way of the electrophoresis pathway. In order to determine their migration distances, for example, for calculating their molecular weights from this image, the calculation is conducted based on the profile of the fluorescence intensity obtained by tracing the electrophoresis pathway from end to end. FIG. 8B shows an exemplary profile of the fluorescence intensity obtained by tracing the image shown in FIG. 8A. This fluorescence intensity profile is displayed on the light intensity profile displaying section 64 of the monitor screen 60. The fluorescence intensity along the center line (as represented by a dashed line in the drawing) of the electrophoresis pathway 12 is made into a graph and displayed. The vertical axis is the light intensity and the horizontal axis is the migration distance, thereby obtaining a profile of the fluorescence intensity. For example, the migration distance of band A shown in FIG. 8A can be obtained as a distance from the initiating point of electrophoresis to the peak point corresponding to band A on the waveform of the light intensity profile.

Figure 9A:
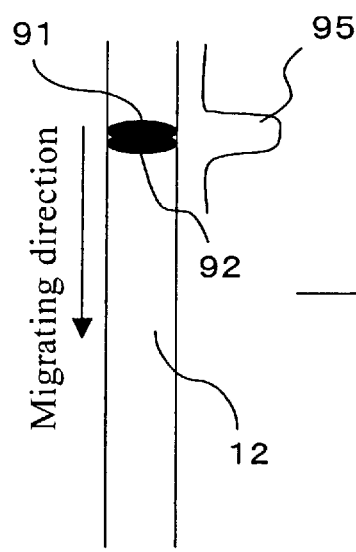
FIGS. 9A to 9C are views showing how bands are separated with the lapse of time.
Figure 9B:
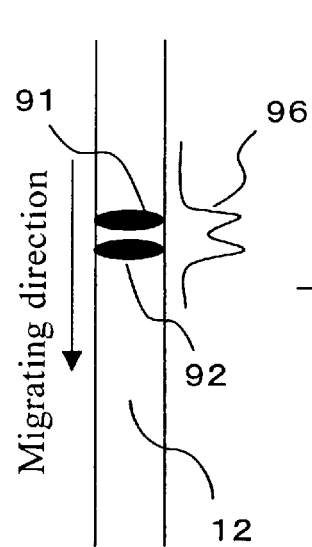
Figure 9C:
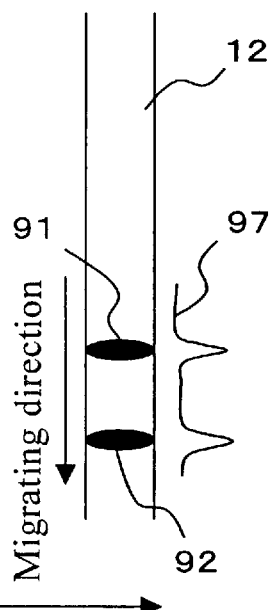

Hereinafter, a method of confirming the separated state will be described. FIGS. 9A to 9C are views showing how bands are separated with the lapse of time. In FIG. 9A, two sample bands 91 and 92 are not yet separated overlapping with each other. This state is represented by a profile 95 with only a single peak, which indicates that it may possibly cause deficiency upon analysis following the reading. Continuing the electrophoresis from the state shown in FIG. 9A, a gap between the two sample bands 91 and 92 becomes wider since the mobility of each of the bands 91 and 92 is in inverse proportion to the logarithm of each of their molecular weights or molecular lengths. With reference to a profile 96 under the state shown in FIG. 9B, the two peaks are not yet sufficiently separated from each other. When electrophoresis is further continued, the sample bands 91 and 92 become completely separated from each other as represented by a profile 97 shown in FIG. 9C.

Hereinafter, an exemplary method for confirming the separated state by actually using the monitor screen will be described with reference to FIGS. 10A–10C and 11A–11C. The separated state is confirmed by using the above-mentioned band selecting tool 74, the rectangular zooming tool 75, the point zooming tool 76 and the partial profile displaying tool 77 provided on the monitor screen. Each of the tools functions as it is selected from a tool box provided above the image displaying section 63.

Figure 10A:
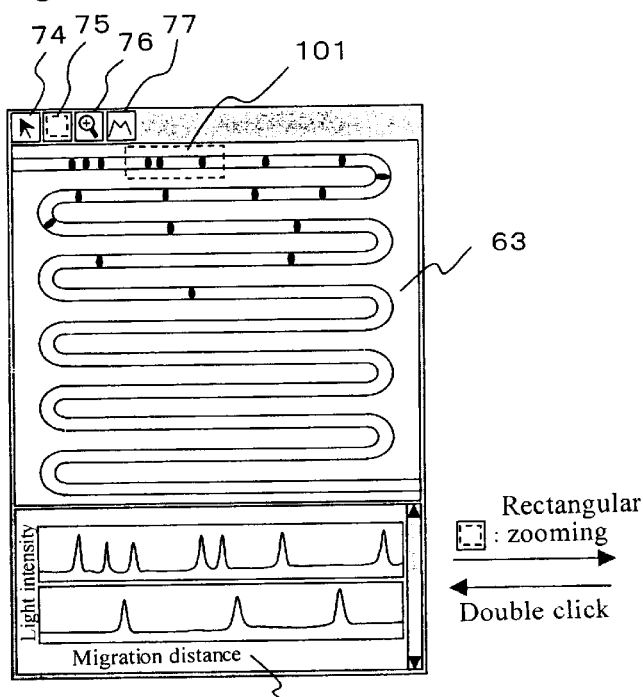
FIGS. 10A to 10C are views for illustrating a way of zooming the image.
Figure 10B:
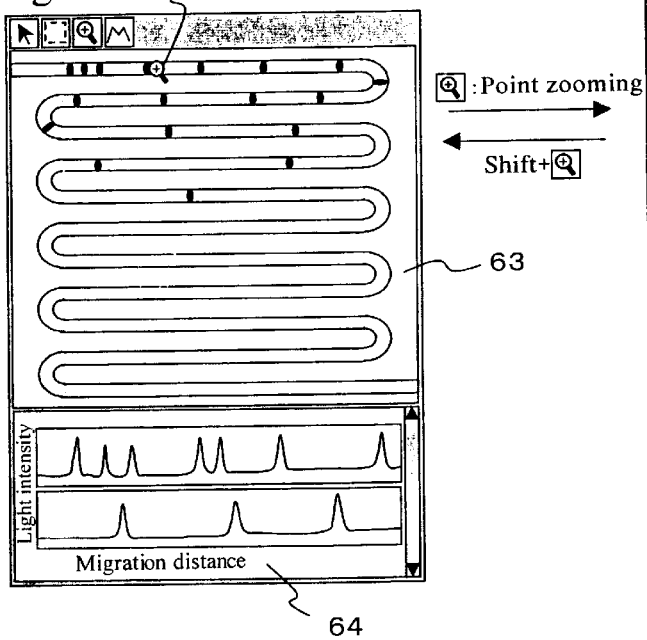
Figure 10C:
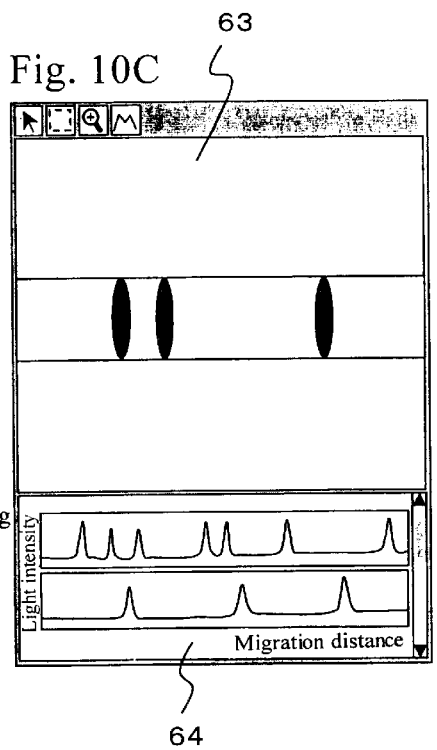

First, a part that needs to be confirmed of its separated state is zoomed in from the whole read image. FIGS. 10A to 10C show a method for zooming the image. There are two types of zooming tools, the rectangular zooming tool 75 and the point zooming tool 76. Where the rectangular zooming tool 75 is used, a rectangular area 101 shown in FIG. 10A is zoomed in and displayed on the entire image displaying section 63 as shown in FIG. 10C. Where the point zooming tool 76 is used, as shown in FIG. 10B, a point selected with a pointing icon 102 becomes the center of the zoomed-in image on the image displaying section 63 where the scale of the image is doubled per click. The zoomed image can be zoomed out to the original image size by double clicking on the image (where the rectangular zooming tool 75 is selected), or by clicking the image while pressing the shift key to zoom out to a ½ scale per click (where the point zooming tool 76 is selected).

Figure 11A:
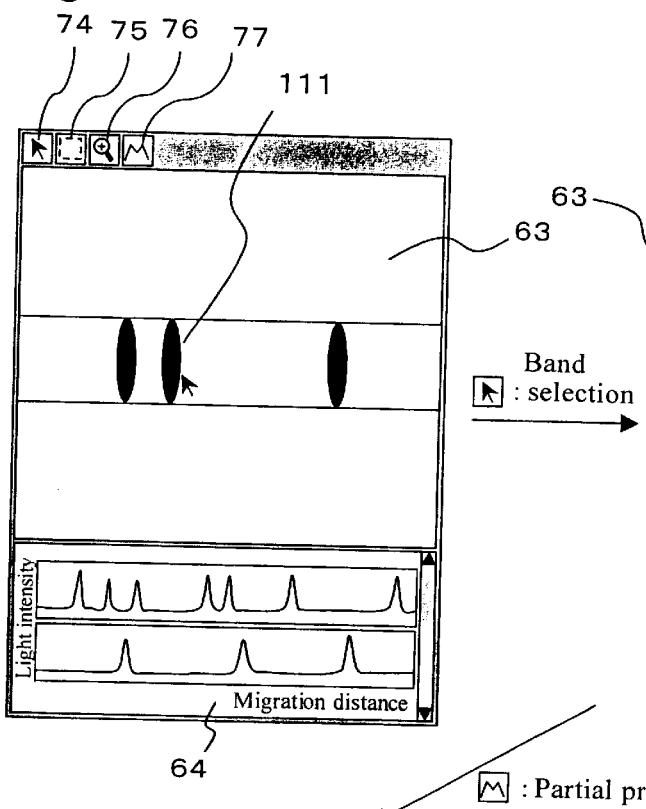
FIGS. 11A to 11C are views for illustrating a relationship between the image and the profile.
Figure 11B:
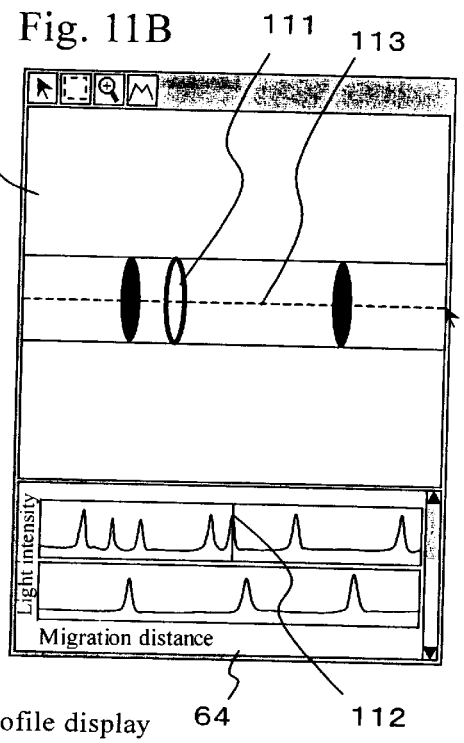
Figure 11C:
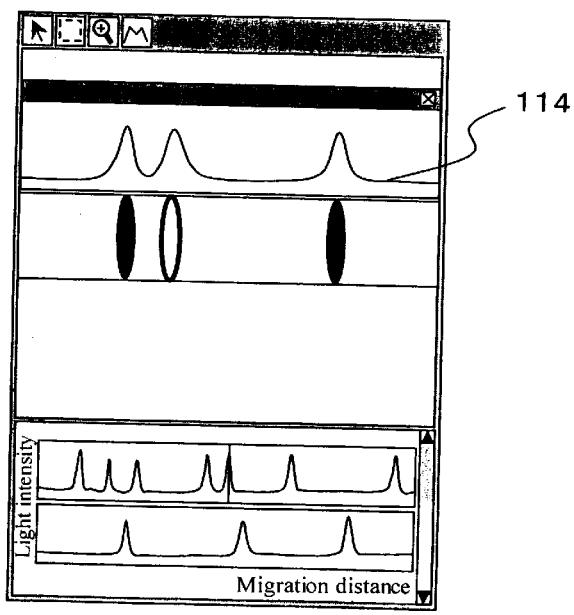
Figure 12A:
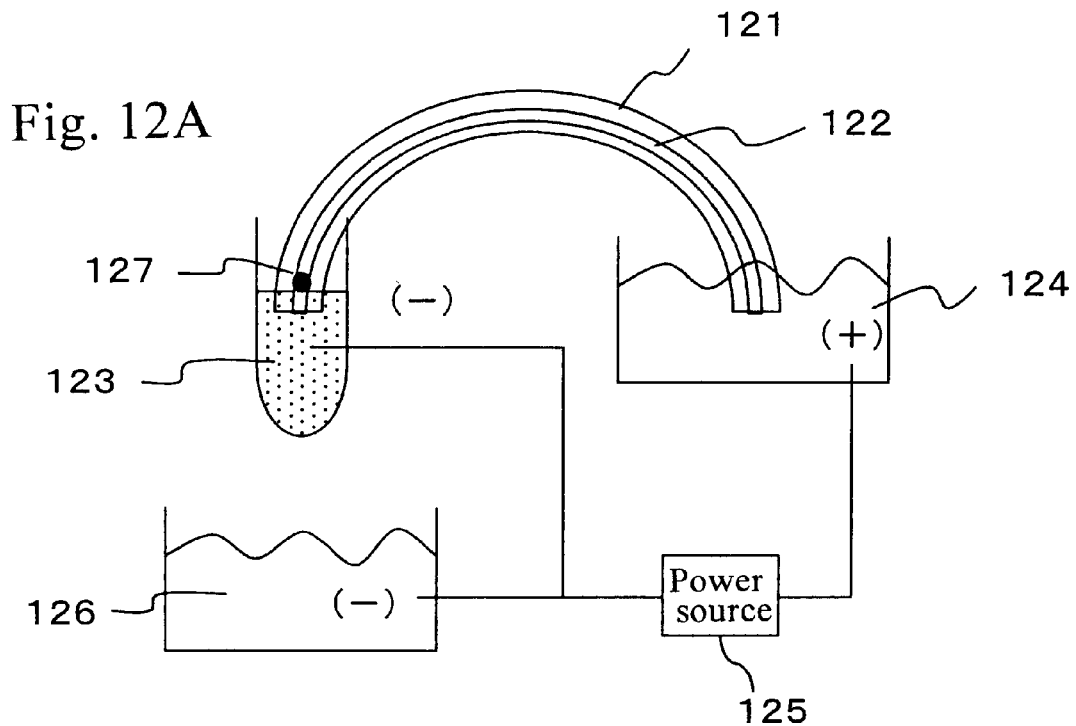
FIGS. 12A and 12B are views for illustrating the principle of a conventional capillary electrophoresis device.
Figure 12B:
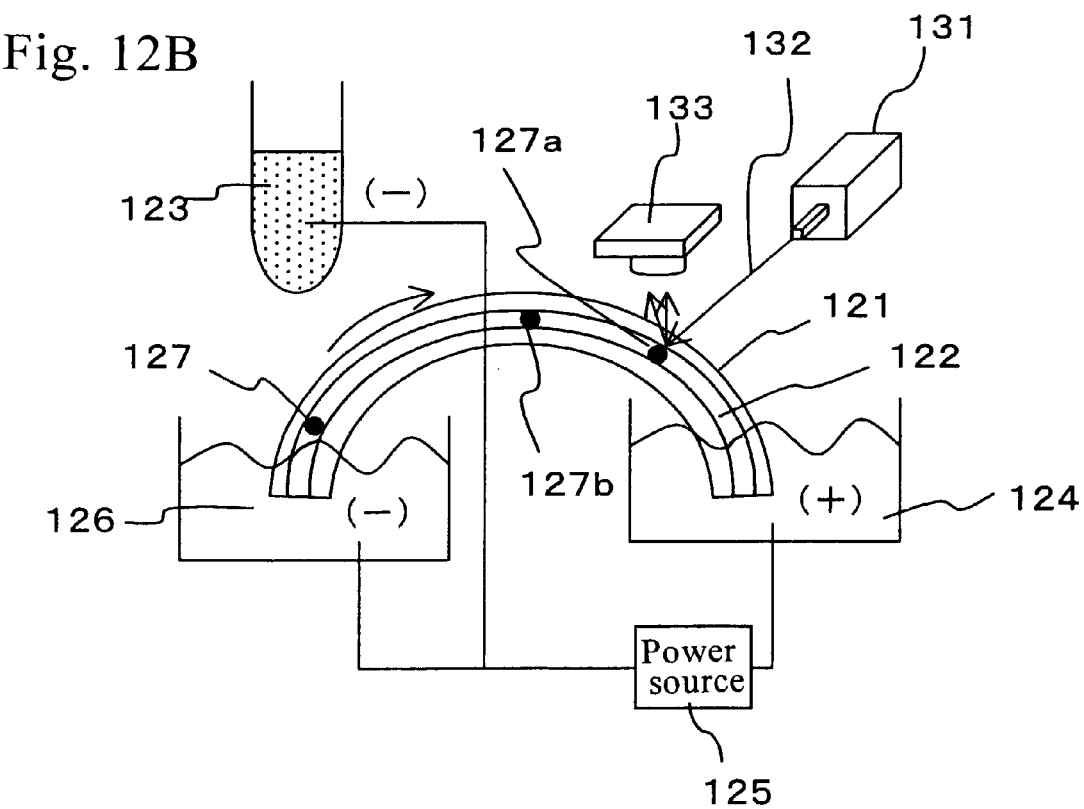

Then, the separated state is confirmed by corresponding the image and the profile of the fluorescence intensity. This method is illustrated in FIGS. 11A to 11C. As shown in FIG. 11A, when a band 111 on the image displaying section 63 is selected with the band selecting tool 74 for confirming its separated state, the light intensity profile on the light intensity profile displaying section 64 automatically scrolls and a mark 112 is provided on the peak on the profile corresponding to the selected band 111. The image and the profile are corresponded with each other based on distance information from the electrophoresis initiating point. Specifically, first the distance of the selected band 111 from the electrophoresis initiating point is obtained. Then, the peak point corresponding to the obtained migration distance on the light intensity profile is provided with the mark 112.

As shown in the image displaying section 63 in FIG. 11B, a line 113 may be drawn with the band selecting tool 74. Then, the partial profile displaying tool 77 may be selected to partially zoom in a profile 114 of the line 113, on the image displaying section 63 or on the profile displaying section 64, thereby enabling confirmation of the separated state in more detail. By the above-described series of operations, an electrophoresis time required for obtaining an optimal separated state (i.e., the state shown in FIG. 9C) may easily be found out.

INDUSTRIAL APPLICABILITY

According to the present invention, the separated state of the sample may be confirmed during the electrophoresis by reading the entire electrophoresis pathway. Accordingly, there is no need of conducting electrophoresis for a long time than is necessary. The electrophoresis may be ended when the sample has sufficiently been separated, and the molecular weight may be determined by measuring the migration distance. As a result, separation and detection may be conducted within a minimum time.

For example, when an electrophoresis pathway with a width of 100 $\mu$m is formed within an area of 2 cm$^2$, the length of the pathway may be about 2 m. Accordingly, a compact device can be realized with an inexpensive temperature controlling system. As a result, experiments utilizing electrophoresis, which require temperature control, such as SSCP method, may easily be conducted which was not practical with conventional capillary electrophoresis devices.

What is claimed is:

1. The electrophoresis device, comprising:
an electrophoresis board provided with a narrow tubular electrophoresis pathway;
a two-dimensional sensor for receiving luminescence emitted from the sample migrating through the electrophoresis pathway;
an image displaying means for displaying an image picked up by the two-dimensional sensor;
a selecting means for selecting at least one of a plurality of sample bands on the electrophoresis image displayed on the image displaying means; and
a light intensity profile zooming means for zooming the profile of the light intensity of the sample band selected by the selecting means,
wherein the sample is simultaneously detected from the entire electrophoresis pathway by the two-dimensional sensor.

2. The electrophoresis device of claim 1, further comprising an excitation light source for radiating excitation light to the entire electrophoresis board, wherein the sample is irradiated by the excitation light source.

3. An electrophoresis device, comprising:
an electrophoresis board provided with a two-dimensional narrow tubular electrophoresis pathway;
an excitation light source for radiating excitation light to the entire electrophoresis board;
a two-dimensional sensor for receiving luminescence emitted from the sample irradiated by the excitation light source and migrating through the electrophoresis pathway,
wherein the sample is simultaneously detected from the entire electrophoresis pathway by the two-dimensional sensor, and
wherein the electrophoresis pathway is shaped as a single spiral or a single wave with a plurality of turns; and
a light intensity profile displaying means for displaying a profile of the intensity of the luminescence detected by the two-dimensional sensor as a function of a distance along the electrophoresis pathway.

4. An electrophoresis device, comprising:
an electrophoresis board provided with a two-dimensional narrow tubular electrophoresis pathway;
an excitation light source for radiating excitation light to the entire electrophoresis board;
a two-dimensional sensor for receiving luminescence emitted from the sample irradiated by the excitation light source and migrating through the electrophoresis pathway,
wherein the sample is simultaneously detected from the entire electrophoresis pathway by the two-dimensional sensor, and
wherein the electrophoresis pathway is shaped as a single spiral or a single wave with a plurality of turns;
an image displaying means for displaying an image picked up by the two-dimensional sensor; and
a light intensity profile displaying means for displaying a profile of the intensity of the luminescence detected by the two-dimensional sensor as a function of a distance from the initiating position of the electrophoresis pathway.

5. The electrophoresis device, comprising:
an electrophoresis board provided with a narrow tubular electrophoresis pathway;
a two-dimensional sensor for receiving luminescence emitted from the sample migrating through the electrophoresis pathway;
an image displaying means for displaying an image picked up by the two-dimensional sensor;

a light intensity profile displaying means for displaying a profile of the intensity of the luminescence detected by the two-dimensional sensor as a function of a distance from the initiating position of the electrophoresis pathway;

a selecting means for selecting at least one of a plurality of sample bands on the electrophoresis image displayed on the image displaying means; and a light intensity profile zooming means for zooming the profile of the light intensity of the sample band selected by the selecting means, wherein the sample is simultaneously detected from the entire electrophoresis pathway by the two-dimensional sensor.

6. The electrophoresis device of claim 5, further comprising an excitation light source for radiating excitation light to the entire electrophoresis board, wherein the sample is irradiated by the excitation light source.

7. An electrophoresis device, comprising:

an electrophoresis board provided with a two-dimensional narrow tubular electrophoresis pathway;

an excitation light source for radiating excitation light to the entire electrophoresis board;

a two-dimensional sensor for receiving luminescence emitted from the sample irradiated by the excitation light source and migrating through the electrophoresis pathway, wherein the sample is simultaneously detected from the entire electrophoresis pathway by the two-dimensional sensor, and wherein the electrophoresis pathway is shaped as a single spiral or a single wave with a plurality of turns;

an image displaying means for displaying an image picked up by the two-dimensional sensor;

a light intensity profile displaying means for displaying a profile of the intensity of the luminescence detected by the two-dimensional sensor as a function of a distance from the initiating position of the electrophoresis pathway;

a selecting means for selecting a sample band on the electrophoresis image displayed on the image displaying means; and a means for indicating a peak point of the light intensity profile corresponding to the sample band selected by the selecting means.

8. An electrophoresis device, comprising:

an electrophoresis board provided with a two-dimensional narrow tubular electrophoresis pathway;

a two-dimensional sensor for receiving luminescence emitted from the sample migrating through the electrophoresis pathway, wherein the sample is simultaneously detected from the entire electrophoresis pathway by the two-dimensional sensor, and wherein the electrophoresis pathway is shaped as a single spiral or a single wave with a plurality of turns; and a light intensity profile displaying means for displaying a profile of the intensity of the luminescence detected by the two-dimensional sensor as a function of a distance along the electrophoresis pathway.

* * * * *